US00PP20139P3

(12) United States Plant Patent
Richards

(10) Patent No.: US PP20,139 P3
(45) Date of Patent: Jun. 30, 2009

(54) ***CORDYLINE AUSTRALIS* PLANT NAMED 'CHARLIE BOY'**

(50) Latin Name: *Cordyline australis*
Varietal Denomination: Charlie Boy

(76) Inventor: Graeme Charles Richards, 7 Cranmore Lane, Holbeach, Lincolnshire, PE12 7Ht (GB)

( * ) Notice: Subject to any disclaimer, the term of this patent is extended or adjusted under 35 U.S.C. 154(b) by 0 days.

(21) Appl. No.: 11/985,486

(22) Filed: Nov. 15, 2007

(65) Prior Publication Data

US 2009/0133175 P1 May 21, 2009

(51) Int. Cl.
*A01H 5/00* (2006.01)

(52) U.S. Cl. ..... Plt./383

(58) Field of Classification Search ..... Plt./383
See application file for complete search history.

*Primary Examiner*—S. B. McCormick Ewoldt
(74) *Attorney, Agent, or Firm*—Fulwider Patton LLP

(57) ABSTRACT

A new and distinct cultivar of *Cordyline* plant named 'Charlie Boy' characterized by cerise pink uniform leaf margins on a brown background, and improved root performance leading to a sturdier, healthier plant.

1 Drawing Sheet

BACKGROUND OF THE NEW PLANT

The present invention relates to a new and distinct cultivar of *Cordyline* plant, botanically known as *Cordyline australis,* and further known by the varietal name 'Charlie Boy.' The new cultivar was collected from a batch of nursery seedlings cultivated through open pollination of various *Cordyline australis* by the inventor, Graeme Charles Richards, in Lincolnshire, England. The parental cultivar is believed to be a combination of *Cordyline australis.* The cultivar has been asexually reproduced via tissue culture reproduction occurring in 2003 in Lincolnshire, England. Seedlings grown from the parental cultivar seeds were planted out and plants with desirable ornamental characteristics were selected. The cultivar was discovered as a naturally occurring whole plant mutation in a commercial planting of the *Cordyline australis* variety, where the parent plants have un-variegated green foliage. The new cultivar is distinguished from other *Cordylines* by its variegated leaves with cerise red edges on a brown background, and enhanced disease resistance. The first plants were weaned out in production testing in 2005 and second generations were weaned in 2006. Continued observation of future generations through asexual reproduction via tissue culture in Lincolnshire, England have confirmed that the distinguishing features of this new cultivar remain true, stable and continuous through successive propagation.

The closest comparator to 'Charlie Boy' known to applicant is *Cordyline australis* 'Red Sensation' (unpatented) which is an erect plant with red/brown foliage. *Cordyline australis* 'Charlie Boy' has cerise pink uniform leaf margins and a hardier constitution for cold and other environmental conditions, different variegation and more vigorous, stronger rooting habit.

SUMMARY OF THE INVENTION

Plants of the cultivar 'Charlie Boy' have not been observed under all possible environmental and cultural conditions. The phenotype of the new cultivar may vary somewhat with variations in environment such as temperature, light intensity, length of day, irrigation amount and frequency, and/or fertilizer rate without, however, any variance in genotype.

The following traits have been repeatedly observed and are determined to be among the unique characteristics of 'Charlie Boy'. These characteristics distinguish 'Charlie Boy' as a new and distinct cultivar from its closest comparator *Cordyline australis* 'Red Sensation' as well as other *Cordyline australis:*

1. Variegated leaves.

Compared to other plants of the *Cordyline* genus, the new *Cordyline* has distinctive variegated leaves.

2. Cerise Red Edged Leaves On Brown Background.

Compared to other plants of the *Cordyline* genus, the new *Cordyline* has distinctive cerise red edged leaves on a brown background.

BRIEF DESCRIPTION OF THE DRAWINGS

The invention is depicted in the accompanying colored photographs in which:

FIG. 1 shows a potted plant illustrating the characteristic foliage.

The photograph depicts the overall appearance of the new *Cordyline,* showing the colors as true as it is reasonably possible to obtain in colored reproductions of this type. Colors in the photograph may differ slightly from the color values cited in the Detailed Botanical Description which more accurately describe the actual colors of the new *Cordyline.*

DETAILED BOTANICAL DESCRIPTION OF THE NEW PLANT

The following detailed description sets forth characteristics of the new cultivar. The data which defines each characteristic was collected from reproductions of the plant grown in an open greenhouse. The plant histories of *Cordyline australis* 'Charlie Boy' were taken on multiple pots containing single plants.

In the following table of plant characteristics, color references where available are made to the Royal Horticultural Society of London Colour Chart, 1995 Edition. The age of the plant described is approximately 1½ years old with measurements taken from mature leaves.

THE PLANT

Classification:

*Botanical.*—*Cordyline australis*.

*Varietal name.*—'Charlie Boy'.

*Parentage.*—Seedling mutation of *Cordyline australis.*

*Asexual propagation.*—Tissue culture.

Form:

*Plant growth rate.*—Approximately 500 mm per annum.

*Growth habit.*—Upright apically dominant with arching leaves.

*Growth type.*—Erect.

*Mean plant height.*—750 mm at age 1½ years.

*Mean plant width.*—1000 mm at age 1½ years.

Stem:

*Scapes.*—Basal foliage.

*Mean stem diameter.*—45 mm at base at 1½ years.

*Stem color.*—Gray brown 197C to 199A/B.

Leaves:

*Leaf color.*—7–10 mm cerise pink edges with brown center.

*Young, upper side.*—Brown 200A; axially striped grayed-brown 182A; margins red 52B.

*Young, under side.*—Brown 200B; axially striped grayed-brown 182A; margins red 52B.

*Mature, upper side.*—Brown 200B; axially striped grayed-brown 182A; margins red 51A/52B.

*Mature, under side.*—Brown 200B; axially striped grayed-brown 182A; margins red 52A/B.

*Leaf shape.*—Arching, sword-shaped leaves on outer with upright in center.

*Mean leaf width.*—15 mm.

*Mean leaf length.*—450 mm.

*Leaf Characteristics.*—Apex — Acute. Margin — Slight undulations. Texture — Smooth, glaucous. Shape — Sword-shaped with no petiole. Average no. of leaves — Approximately 70–80 on an 18 month old plant. Venation pattern — Parallel. Venation color. — Indistinguishable from foliage coloration.

Inflorescence: N/A (No flowers observed to date)

Other characteristics:

*Temperature tolerance.*—Tolerates low temperatures to at least −8° C. and high temperatures to at least 33° C.

GENERAL CHARACTERISTICS

'Charlie Boy' is primarily distinguished from other cultivars of *Cordyline* genus by its variegated cerise foliage. 'Charlie Boy' has an upright growth habit with smooth, glaucous leaves with slight undulations on their margins.

What is claimed is:

1. A new and distinct *Cordyline australis* plant named 'Charlie Boy' substantially as illustrated and described.

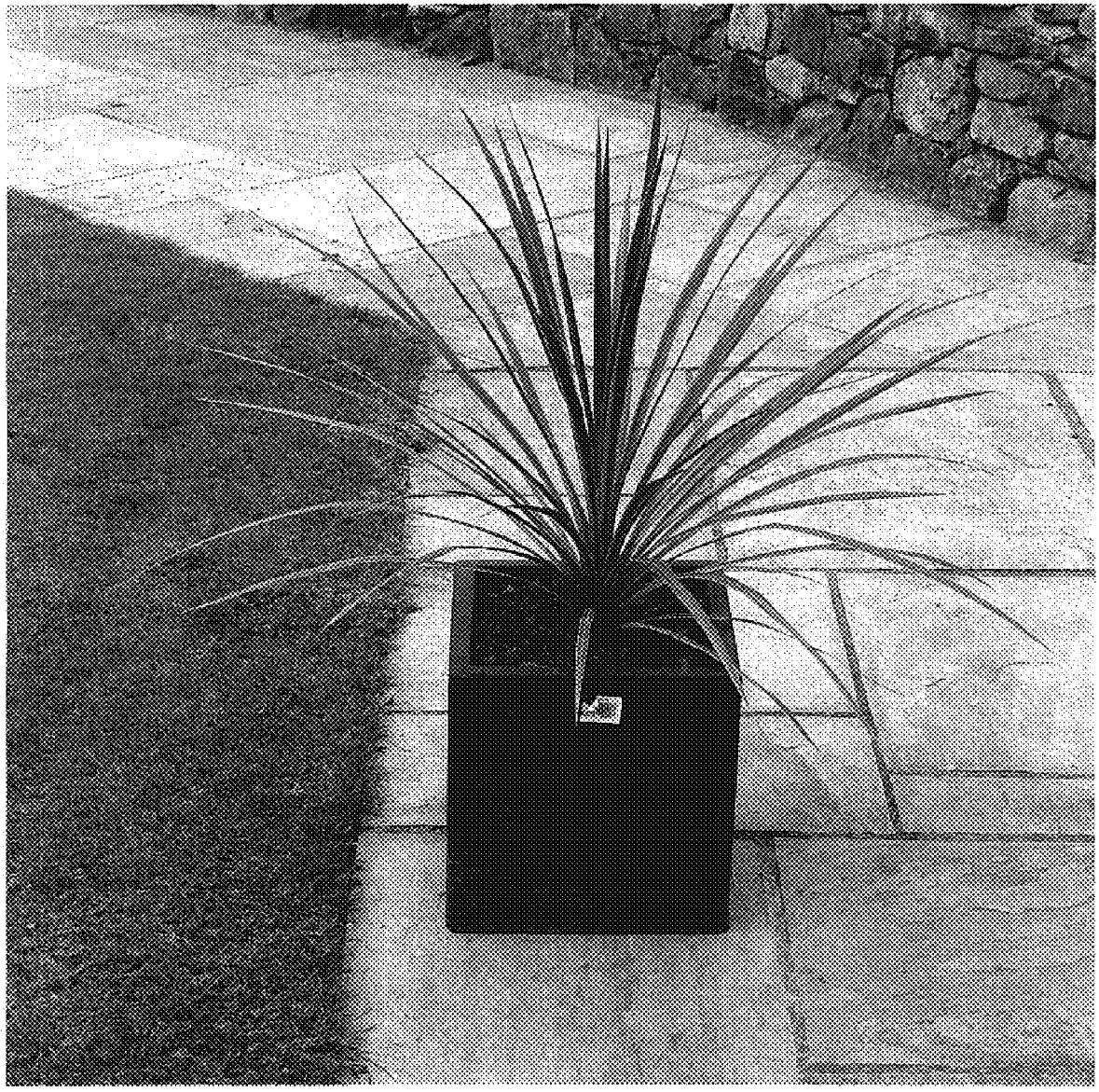

* * * * *